United States Patent
Blomsma et al.

(10) Patent No.: US 7,702,071 B2
(45) Date of Patent: Apr. 20, 2010

(54) METHOD FOR PERFORMING POWER DIFFRACTION ANALYSIS

(75) Inventors: Erwin Blomsma, Haarlem (NL); Adriaan Jan van Langevelde, Almere (NL)

(73) Assignee: Avantium International B.V., Amsterdam (NL)

( * ) Notice: Subject to any disclaimer, the term of this patent is extended or adjusted under 35 U.S.C. 154(b) by 0 days.

(21) Appl. No.: 10/485,927

(22) PCT Filed: Jan. 15, 2003

(86) PCT No.: PCT/EP03/00451

§ 371 (c)(1),
(2), (4) Date: Feb. 3, 2004

(87) PCT Pub. No.: WO03/060497

PCT Pub. Date: Jul. 24, 2003

(65) Prior Publication Data

US 2005/0002487 A1    Jan. 6, 2005

Related U.S. Application Data

(60) Provisional application No. 60/347,891, filed on Jan. 15, 2002.

(30) Foreign Application Priority Data

Jan. 15, 2002    (EP) .................................. 02075149

(51) Int. Cl.
*G01N 23/205* (2006.01)
*G01N 23/207* (2006.01)
(52) U.S. Cl. ............... 378/75; 378/73; 378/79
(58) Field of Classification Search .................. 378/71, 378/73, 75, 77, 79
See application file for complete search history.

(56) References Cited

U.S. PATENT DOCUMENTS 3,527,942 A    9/1970    Roe et al.

(Continued)

FOREIGN PATENT DOCUMENTS

DE    1 598 413    4/1970

(Continued)

OTHER PUBLICATIONS

Opposition paper filed against corresponding European granted application, EP 1 466 166.

(Continued)

*Primary Examiner*—Irakli Kiknadze
*Assistant Examiner*—Thomas R. Artman
(74) *Attorney, Agent, or Firm*—Hoffmann & Baron, LLP

(57) ABSTRACT

A method for successively performing a powder diffraction analysis of at least two powder samples being contained in sample holding means. Use is made of an apparatus comprising:—a source of radiation being adapted to direct a radiation beam to a power sample,—a detector for detecting diffraction radiation of a powder sample,—a drive means associated with said sample holding means for effecting a movement of an irradiated powder sample during irradiation and detection. The method comprises the steps of irradiating a powder sample and detecting the diffraction radiation of the powder sample, arranging a further powder sample such that said radiation beam is directed to said further powder sample, and irradiating said further powder sample and detecting the diffraction radiation of said further sample. During irradiation and detecting of each sample the drive means effect a movement of the irradiated sample with respect to the radiation beam for the purpose of improving particle statistics. The sample holding means comprise a common multiple samples holder holding said at least two powder samples. Said drive means effect, during irradiation and detection of a sample contained in said common multiple samples holder, a movement of said common multiple samples holder with respect to the radiation beam.

32 Claims, 6 Drawing Sheets

U.S. PATENT DOCUMENTS

| | | | | |
|---|---|---|---|---|
| 4,016,420 | A * | 4/1977 | Rieder | 378/77 |
| 4,199,678 | A * | 4/1980 | Ladell | 378/75 |
| 4,413,354 | A * | 11/1983 | Manners | 378/81 |
| 5,359,640 | A | 10/1994 | Fink et al. | |
| 5,878,106 | A | 3/1999 | Fujiwara | |
| 6,111,930 | A | 8/2000 | Schipper | |
| 6,400,797 | B1 | 6/2002 | D'Amico | |
| 6,507,636 | B1 | 1/2003 | Lehmann | |
| 6,605,473 | B1 * | 8/2003 | Hajduk et al. | 436/174 |
| 6,738,717 | B2 * | 5/2004 | Saito | 702/40 |
| 6,882,739 | B2 * | 4/2005 | Kurtz et al. | 382/109 |
| 2002/0067800 | A1 * | 6/2002 | Newman et al. | 378/73 |

FOREIGN PATENT DOCUMENTS

| | | |
|---|---|---|
| NL | 7416557 | 6/1976 |
| WO | WO 99/ 51972 | 10/1999 |
| WO | WO 00/36405 | 6/2000 |
| WO | WO 02/057763 | 7/2002 |

OTHER PUBLICATIONS

Klein et al., "Combinatorial Material Libraries on the Microgram Scale with an Example of Hydrothermal Synthesis," Angew. Chem. Int. Ed (1998) 37, 3369-3372.

Isaacs et al., "Synchrotron x-ray microbeam diagnostics of combinatorial synthesis," Appl. Phys. Lett (1998) 73, 1820-1822.

Bruker AXS, "Diffraction Solutions for Combinatorial Screening—D* Discover with GADDS" (2000).

Bruker AXS, "Diffraction Solutions for material research—D8 Discover" (1998).

Bruker AXS, "Lab Report XRD 22—GADDS: Improved Sampling Statistics with Rotation/Oscillation Stage" (2000).

B.D. Cullity, "Elements of X-ray Diffraction" (Addison-Wesley, Reading, Massachusetts: 1978), pp. 1-230.

Vaudin et al., "A Method for Crystallographic Texture Investigations Using Standard X-ray Esquipment," J. Mater Res. (1998) 13, 10, 2910-2919.

Rapid Screening of Polymorphs by Diffraction Methods, Christian W. Lehmann, Sep. 1999, MPI fürKohlenforschung—Chemical Crystallography.

* cited by examiner

METHOD FOR PERFORMING POWER DIFFRACTION ANALYSIS

CROSS-REFERENCE TO RELATED APPLICATIONS

This application is the National Stage of International Application No. PCT/EP03/00451, filed Jan. 15, 2003, which claims the benefit of U.S. Provisional Application No. 60/347,891, filed Jan. 15, 2002, and of European Application No. EP 02075149.1, filed Jan. 15, 2002, the contents of which are incorporated by reference herein.

FIELD OF THE INVENTION

The present invention relates a method for successively performing a powder diffraction analysis of at least two powder samples being contained in sample holding means.

Scattering of incident radiation such as X-rays, gamma rays, cathode rays, etc. from a sample of material can yield information about the atomic structure of the material. When such a beam of radiation strikes a sample, a pattern of diffracted radiation is created, which has a spatial intensity distribution that depends on the wavelength of the incident radiation and the atomic structure of the material and that can be recorded on a suitable detector such as a point detector, a 1D array detector or a 2D detector. Diffraction analysis is the method of choice for studying crystalline materials, crystallisation behaviour and liquid, gel or solid phase, or phase transitions of materials.

BACKGROUND OF THE INVENTION

DE 15 98 413 discloses an apparatus wherein a single sample is held in a sample holder. During the irradiation and detection of diffracted radiation, the drive means associated with the single sample holder cause the sample to perform a translation in combination with a rotation of the sample about an axis at right angles to the irradiated plane of the sample. The purpose of the sample movement during the irradiation and detection is to improve the so called "particle statistics" and to obtain more reliable reflection intensities, or intensities with reduced standard deviation.

A problem that is encountered when using the apparatus of DE 15 98 413 is that it is time consuming when a plurality of powder samples have to be analysed. This problem is particularly pertinent in case of high throughput experimentation. According to the known method each powder sample is prepared one by one in an associated single sample holder and placed in the apparatus for performing the powder diffraction analysis. Then the apparatus is set and aligned, whereupon irradiation and detection take places. Subsequently, the powder is removed and a further powder sample is prepared and so on. This results in an ineffective way of working and thus in a considerable loss of time.

In U.S. Pat. No. 6,111,930 a powder diffraction analysis apparatus is disclosed having a sample changer. Said changer has a plurality of ring-shaped containers each for receiving a sample. The containers are mounted on a linear magazine, such that the samples can be successively brought into the irradiation beam. This known apparatus allows for the spinning of ring-shaped container holding the irradiated sample about an axis perpendicular of the sample surface, which is a common approach to improve the particle statistics.

A problem that is encountered with other known powder diffraction analysis equipment using a 2D detector is that during detection of the diffraction radiation, single diffraction spots and arcs are often observed instead of rings, especially when organic crystalline material (such as pharmaceuticals) is irradiated. This may be the result of the fact that not all lattice planes of the crystalline powder material have been in reflection or not for the same time or same amount, because the crystals were not random oriented or only a few crystals were present. As a result, the peak intensities of the powder diffraction patterns are not correct, and no representative 1D-powder diffraction pattern (intensity vs. diffraction angle $2\theta$) is created after integration of the detected 2D diffraction patterns causing problems during comparison of diffraction patterns for identification.

OBJECT OF THE INVENTION

It is an object of the present invention to provide a method for performing powder diffraction analysis of a plurality of powder samples in a time effective way.

It is a further object of the present invention to allow a diffraction pattern to be obtained with correct reflection intensities.

SUMMARY OF THE INVENTION

The above and other objects can be achieved by a method according to the present invention for successively performing a powder diffraction analysis of at least two powder samples being contained in sample holding means, wherein use is made of an apparatus comprising:
- a source of radiation being adapted to direct a radiation beam to a powder sample,
- a detector for detecting diffraction radiation of a powder sample,
- a drive means associated with said sample holding means for effecting a movement of an irradiated powder sample during irradiation and detection, wherein the method comprises the steps of:
irradiating a powder sample and detecting the diffraction radiation of the powder sample, arranging a further powder sample such that said radiation beam is directed to said further powder sample, and irradiating said further powder sample and detecting the diffraction radiation of said further sample, wherein during irradiation and detection of each sample the drive means effect a movement of the sample with respect to the radiation beam for the purpose of improving particle statistics.

The method is characterised in that the sample holding means comprise a common multiple samples holder holding said at least two powder samples.

Using the method according to the invention a plurality of powder samples may be analysed in a time effective way. The powder samples may be all prepared at the same time in said common multiple samples holder, and are be placed at the same time in the apparatus for performing a powder sample diffraction analysis. Then, the powder samples are all analysed one by one, without the need to remove an earlier powder sample and resetting and fine tuning the apparatus as in DE 15 91 413.

A "powder sample" is defined herein as a powder sample of a compound of which the diffraction or crystallisation behaviour is to be determined. Such a compound may be a chemical substance, or a mixture of different substances. Also, at least one crystal form of the compound may be known or expected to exist. A compound of the invention may comprise an organic or organo-metallic molecular compound, such as a pharmaceutically active molecule or catalyst-ligand complex or a dimer, salt, ester, solvate or functional part thereof. A powder sample of the present invention may also comprise a biomolecule, for instance a nucleic acid (such as DNA, RNA and PNA), a polypeptide, peptides, glycoprotein and other proteinaceous substances, a lipoprotein, protein-nucleic acid complex, carbohydrate, biomimetic or a functional part, derivative and/or analogue thereof.

It is to be noted that the powder sample may indeed be in the form of a powder. The person skilled in the art of diffraction analysis understands, however, that a "powder sample" also includes a number of crystals which are contained in a solid material, such as is the case for metals, polymers, etc. Thus, in the latter case, the powder sample appears as a solid material in one piece.

According to the present invention "powder diffraction analysis" comprises both transmission and reflection diffraction analysis. Transmission and reflection diffraction analysis are well known in the art an do not require further explanation.

According to the present invention, with "common multiple samples holder" is meant any sample holder capable of holding at least two powder samples, either in form of a powder or in form of a solid material in one piece, such that the irradiated sample as well as the other sample(s) in said holder are subjected by the drive means to the prescribed movement.

The common multiple samples holder may be a plate, e.g. similar to a microtiter plate, having a plurality of wells, each for receiving a powder sample. Preferably said wells are arranged in an array, more preferably a 2D-array. Examples of such sample holders are 8 by 12 mm up to 32 by 48 mm, with orthogonal centre to centre distance varying from 2 to 10 mm between the wells.

Preferably the common multiple samples holder is fabricated from material that is translucent to the irradiation beam, e.g. X-rays in the case of X-ray diffraction.

The common multiple samples holder is preferably chemically inert to the substances and solvents employed.

The common multiple samples holder is preferably also transparent to visual light (ca 200 nm to 1000 nm) to allow visual or optical inspection.

The common multiple samples holder is preferably also capable of transferring heat, thereby allowing for temperature variations.

Of course, the apparatus may be provided with means for controlling and/or adjusting the atmosphere conditions in or directly above the wells. For this purpose the sample holder is for instance fitted with sealing devices or sealing substances which seal off individual wells or groups of wells. Balls, plates, caps, inert liquids like paraffin oil, silicon oil, etc. can be provided for said sealing purposes. In this respect it is noted that the sealing devices and/or sealing substances do not necessarily (and preferably do not) attach the powder sample to the sample holder, but are provided for controlling the atmosphere in or directly above an individual well or a group of wells.

According to the present invention, with "suitable radiation" any radiation is meant which can be used for performing a transmission or reflection diffraction analysis (preferably transmission diffraction analysis) of the powder samples, such as X-rays, gamma rays, and cathode rays. Preferably as the radiation X-rays are used.

In a possible embodiment the drive means are associated with said samples holder, and the drive means effect, during irradiation and detection of a sample contained in common multiple samples holder, a movement of said common multiple samples holder with respect to the irradiation beam.

In a further embodiment the drive means are (also) connected to radiation source and detector for the purpose of effecting the movement of the samples holder with respect to the radiation beam.

Preferably the the irradiated sample has a centre and the movement includes a predetermined variation of the orientation of an axis perpendicular to a sample plane and intersecting the centre of the irradiated sample with respect to the radiation beam.

Preferably the movement includes a precession movement, a translation, a tilting or a combination thereof of said common multiple samples holder with respect to the radiation beam.

According to a first preferred embodiment of the method, the common multiple sample holder is subjected by the drive means to a precession movement with respect to the radiation beam. Herewith, the irradiated sample also performs said precession movement and thus account can be taken of different orientations of the crystals in said sample.

"Precession movement" is a technique that is well known in the art for single crystal measurement techniques. Detailed explanation of an exemplary precession movement technique may for example be found in 'Fundamentals of Crystallography', edited by C. Giacovazzo, pp. 254–259 (1991) or in various internet-sites of Astrophysics sciences, the latter explaining the precession movement of the equinox.

In this respect it is noted that, although it is known since the early 1940's to use precession movements for single crystal measurements, this technique has not been used for powder sample measurements. Further, in single crystal measurements, precession movement is used to obtain single crystal unit cell parameters and not for performing a powder diffraction analysis which is completely different.

It is noted that the precession movement can be conducted in part.

According to a second preferred embodiment of method, the common multiple samples holder is subjected to a translation with respect to the radiation beam during the irradiation and detection of a sample, i.e. the normal to the irradiated sample surface is translated with respect to the radiation beam, in parallel orientation to the radiation beam, allowing other crystals in the powder sample to be analysed.

Preferably the holder is such that all sample surfaces to be irradiated lie in a common plane.

Herewith powder diffraction rings may be obtained instead of single diffraction spots, as the particle statistics is significantly improved. Particle statistics is a term known in the art. With achieving 'improved particle statistics' is meant obtaining a powder diffraction pattern with more reliable reflection intensities, or intensities with reduced standard deviation.

According to a particularly preferred embodiment, the common multiple sample holder is subjected to a combination of a precession movement and a translation during the irradiation and detection of a sample. Herewith at the same time improved particle statistics can be obtained and account can be taken of different orientations of the crystals in a surprisingly simple manner.

In a further embodiment the common multiple samples holder is subjected to a so-called omega-rotation, wherein the normal to the irradiated sample plane performs a tilting movement with respect to the radiation beam. If one would conduct a series of such tilting movements in combination with a suitable (stepwise) rotation of the holder the man skilled in the art will understand that the effect similar to performing a precession movement can be obtained.

The invention relates to an apparatus for performing powder diffraction analysis of multiple powder sample according to the above disclosed method.

DETAILED DESCRIPTION OF PREFERRED EMBODIMENTS

Figure 1:
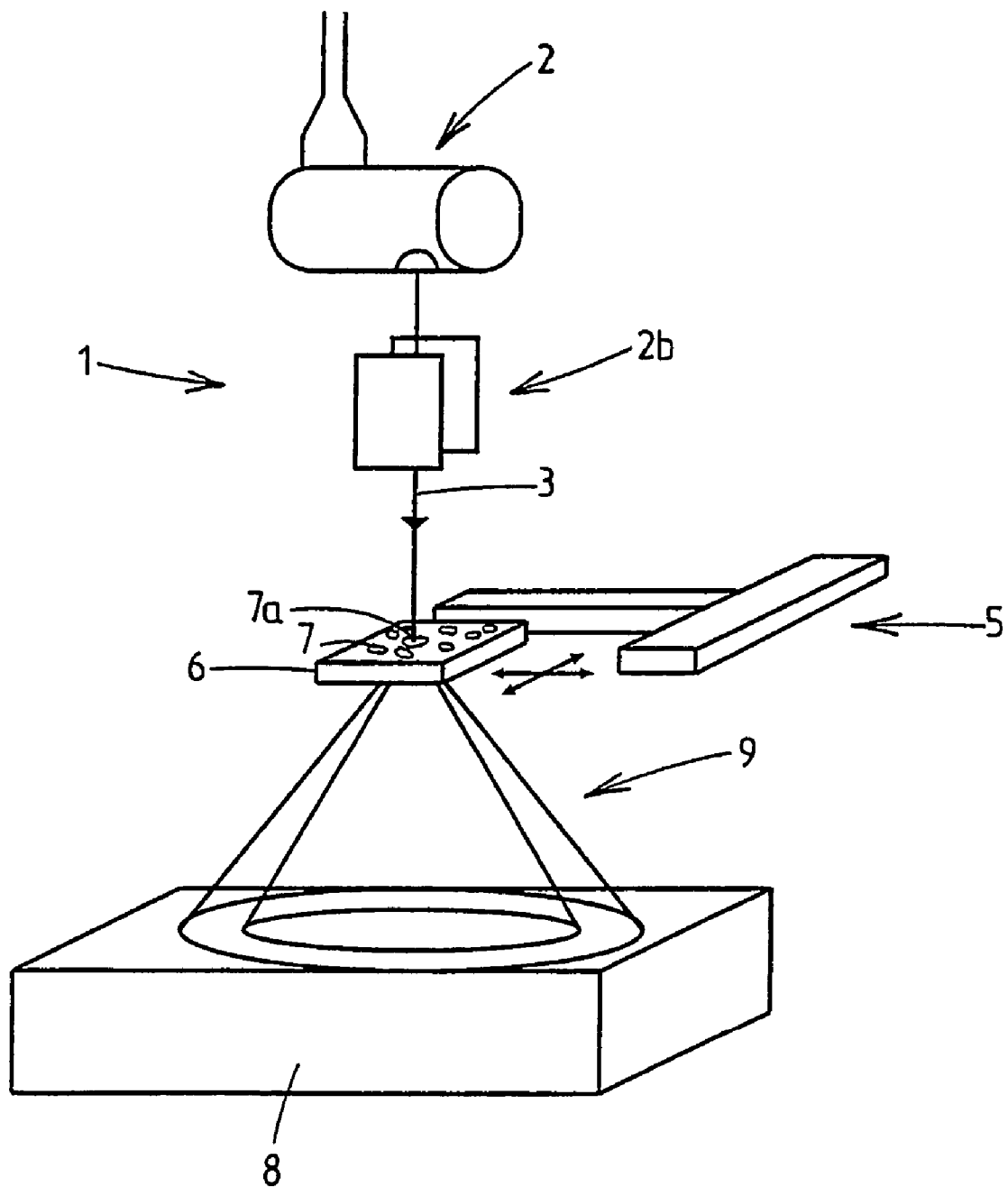
FIG. 1 shows schematically a first embodiment of a transmission mode X-ray diffraction analysing apparatus to be used in accordance with the method of the invention.

FIG. 1 shows a diagram of an exemplary transmission mode X-ray diffraction analysing apparatus 1. The apparatus 1 comprises a source 2 adapted to generate an intense X-ray radiation beam 3, such as a conventional X-ray tube. The beam 3 is passed through a focussing device 2b.

Figure 2:
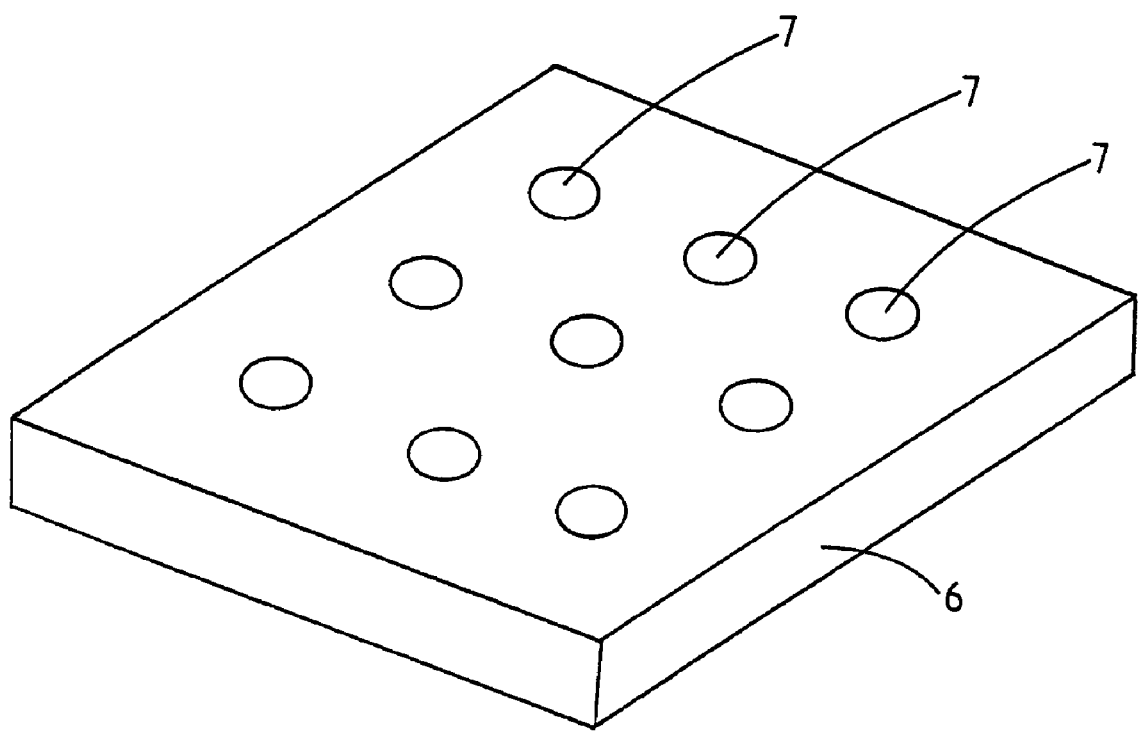
FIG. 2 shows an example of a common multiple sample holder to be used in the method according to the invention.

The apparatus 1 further includes a drive means 5, which is adapted to receive a common multiple samples holder 6. In said sample holder 6, of which an example is shown in FIG. 2, a plurality of powder samples 7 are contained, e.g. in a two-dimensional array of wells.

The radiation beam 3 strikes a single powder sample 7a.

The apparatus 1 further includes a diffracted radiation detector 8 for the detection of diffracted radiation 9 passed through the powder sample 7a.

In the shown embodiment the source 2 of X-ray radiation is located above the powder samples 7, but the inverted and other arrangements are also possible.

The detector 8 may be any suitable detector, such as a stimulable phosphor image plate detector. Preferably the detector 8 is a position sensitive 2D radiation detector.

The drive means 5 are designed in FIG. 1 to cause a displacement of the common multiple samples holder 6 such that the radiation beam 3 successively strikes each of the samples 7 in said holder 6 and are usually motorised as well as automated.

The drive means 5 are further designed such that during the irradiation of a sample 7 and the detection and recording of the diffracted radiation, the common multiple samples holder 6 is caused to effect a translation such that the radiation beam 3 strikes different points of said sample 7 while maintaining a parallel orientation between the beam 3 and the normal to the irradiated surface of the sample 7.

As the analysis of a sample is completed, the drive means caused the sample holder 6 to move such that the beam 3 can irradiate a further sample 7. This sequence is continued preferably in an automated manner until all samples 7 have been analysed.

Figure 3:
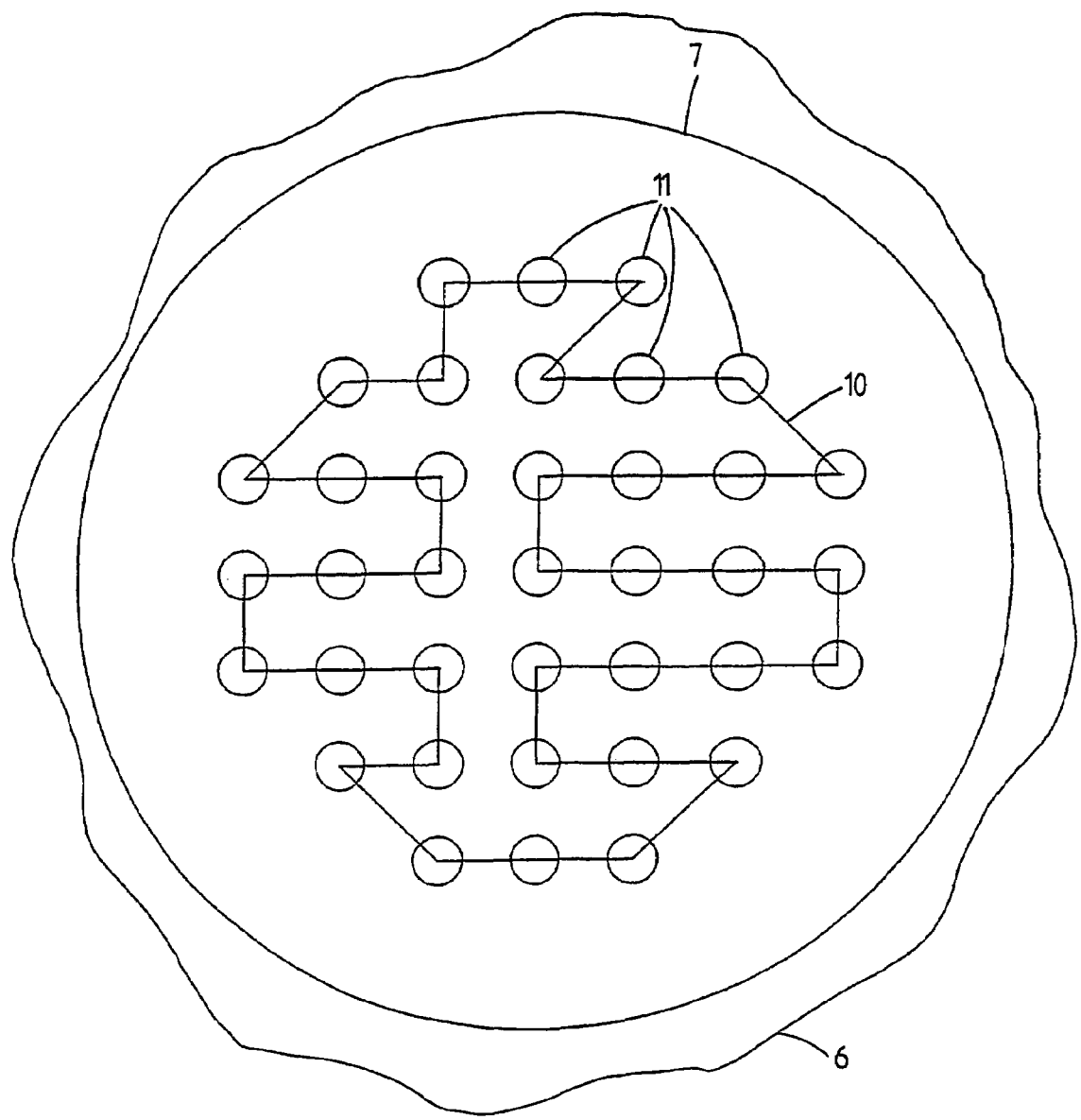
FIG. 3 shows a schematic diagram of an exemplary path that the radiation beam may follow over one powder sample during irradiation and detection, using a translation movement.

FIG. 3 shows a schematic diagram of an exemplary path that the radiation beam 6 of FIG. 1 may follow during irradiation of one of the powder samples 7 in the sample holder 6 in FIG. 2 using translation, preferably in a stepwise manner. The path of the diffraction radiation obtained by the translation is denoted with 10. Herewith several areas 11 of the powder sample 7 are irradiated, whereby diffraction rings (see FIG. 5) instead of diffraction arcs or spots (see FIG. 4) may be obtained.

Figure 4:
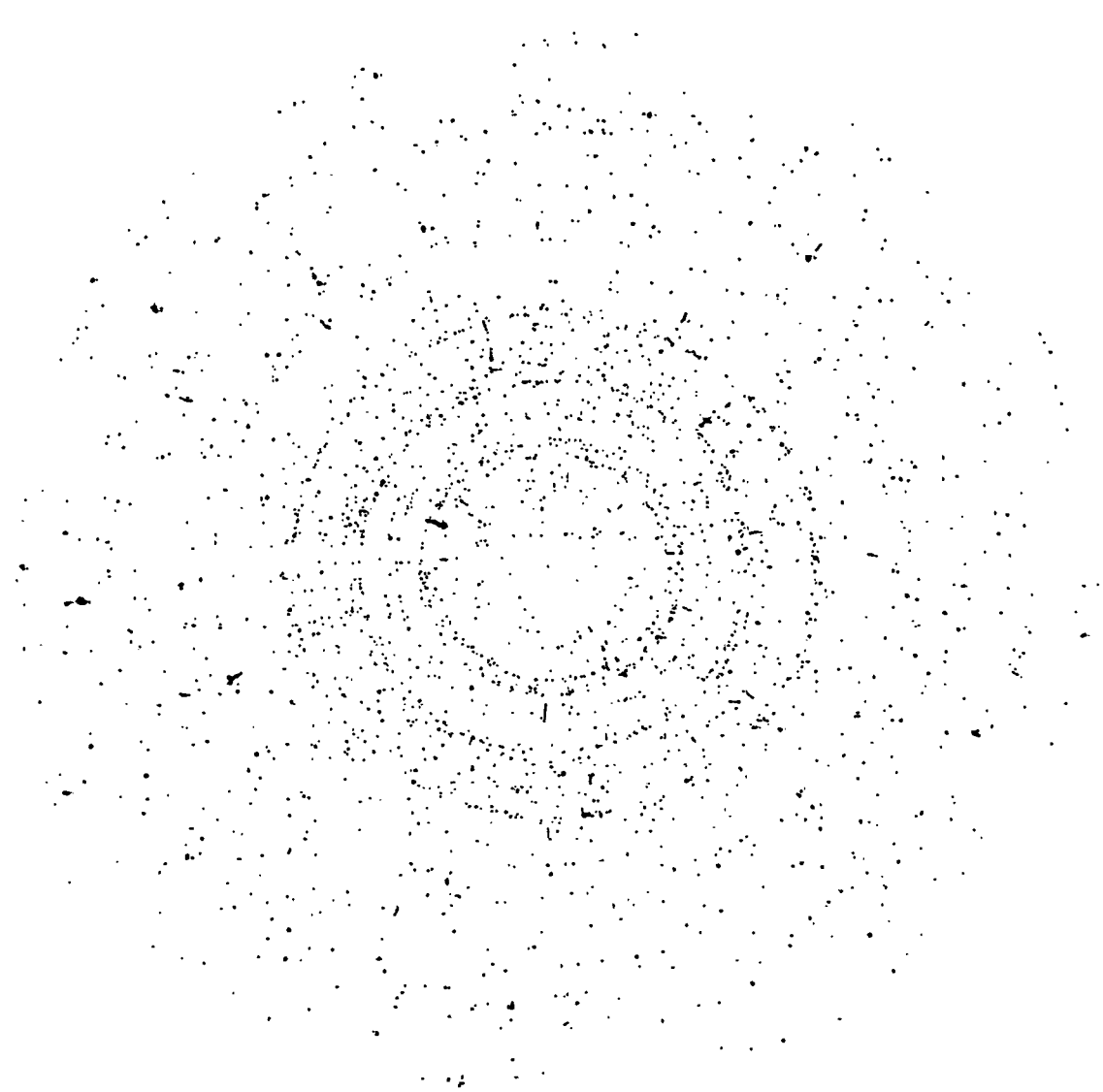
FIG. 4 shows a result of a known powder diffraction measurement, wherein single diffraction spots are obtained.

FIG. 4 shows a two-dimensional X-ray diffraction image of manually crunched sugar using a 0.4 mm X-ray beam fixed at the centre of the sample according to the state of the art.

Figure 5:
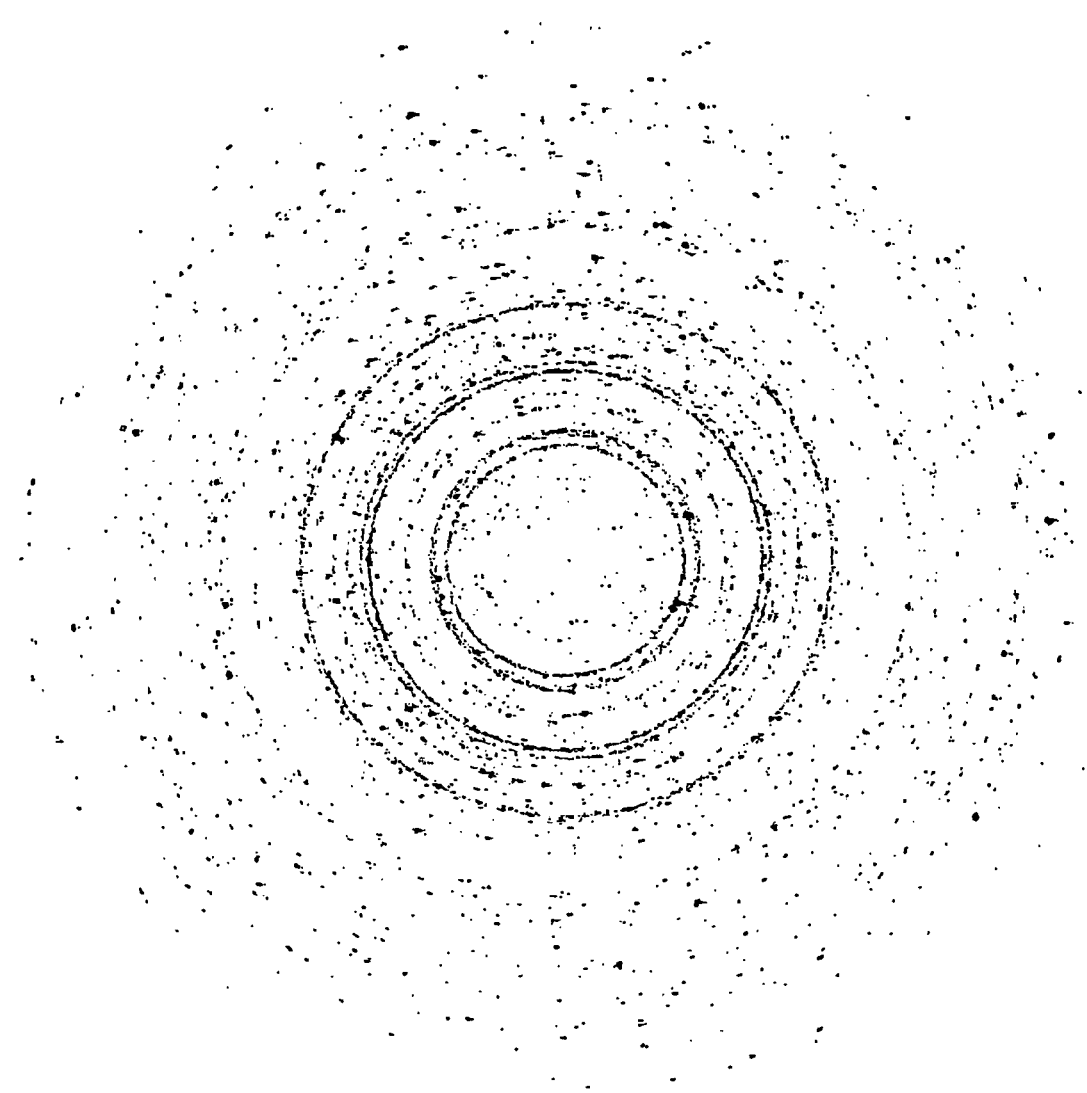
FIG. 5 shows a result of a powder diffraction measurement obtained using the method according to the present invention, using a translation, wherein powder diffraction rings are obtained.

FIG. 5 shows a two-dimensional X-ray diffraction image of the same crunched sugar as in FIG. 4 using a 0.4 mm X-ray beam while the radiation beam is subjected to a translation according to the invention.

Figure 6:
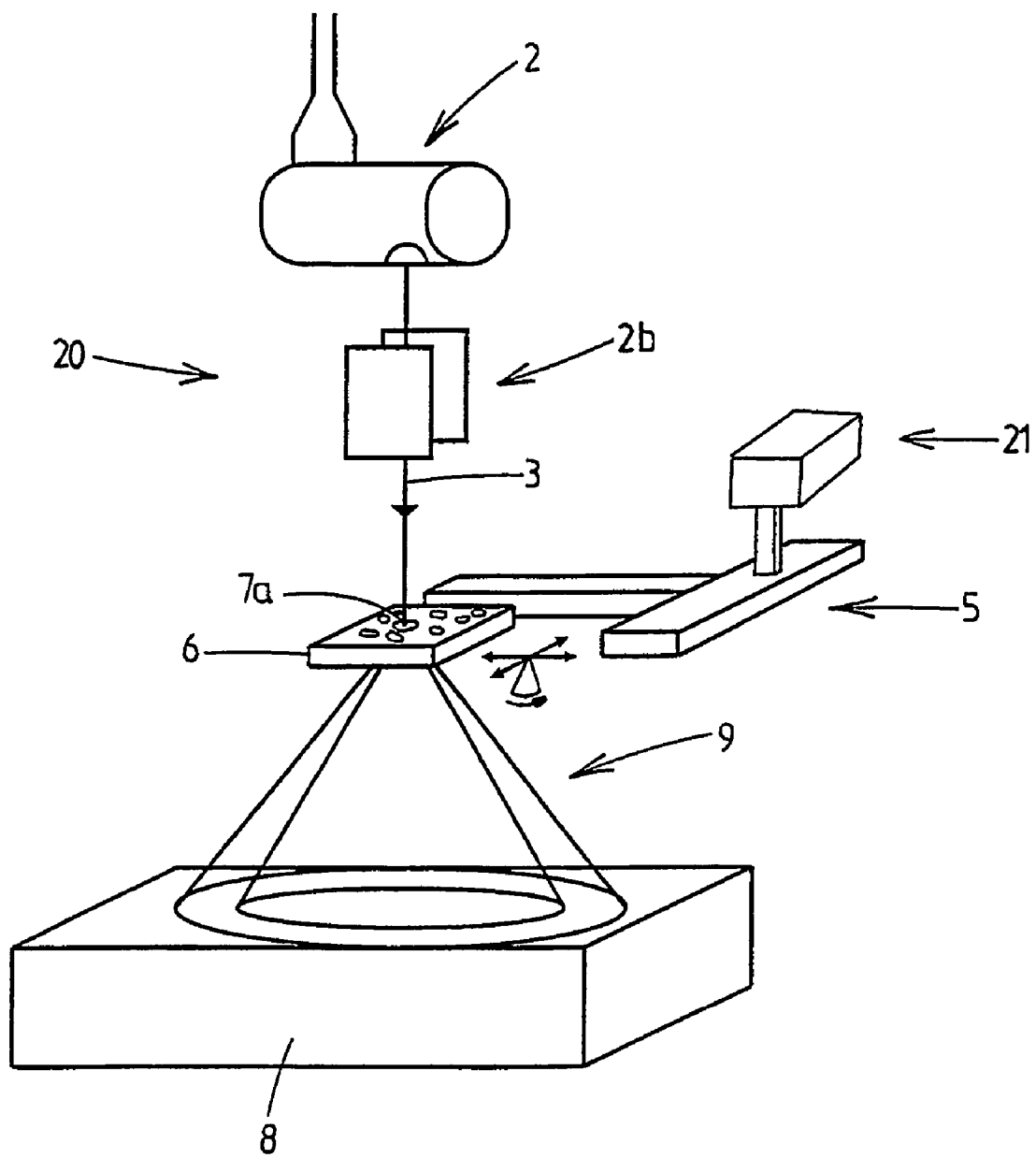
FIG. 6 shows a second embodiment of a transmission mode X-ray diffraction analysing apparatus to be used in accordance with the method of the invention.

FIG. 6 shows a second embodiment of an apparatus 20 for performing radiation diffraction analysis of multiple samples according to the invention. In FIG. 6 parts corresponding to parts of the apparatus of FIG. 1 have been given the same reference numerals.

The drive means associated with the sample holder 6 includes translation drive means 5, which allow for a translation as explained with reference to FIG. 1.

The drive means in FIG. 6 also include a precession drive means 21 which allows for a precession movement of the sample holder 6, such that the normal to the sample plane of a powder sample 7 precesses about the radiation beam 6.

In the shown embodiment of transmission diffraction, this means that the normal to the sample plane of the irradiated powder sample 7 revolves about the radiation beam 3, while keeping e.g. a constant angle, the "precession angle". The normal to the sample plane thus follows a cone-shaped path relative to the radiation beam 3. The movement can consist of only a part of said cone-shaped path. Also the movement is not restricted to a constant precession angle. Also, the precession movement may be effected as a series of tilting movements in combination with suitable (stepwise) rotation of the sample holder 6 as will be apparent to the man skilled in the art.

The drive means 5 and 21 thus allow for a combination of a translation and precession movement during the analysis of a sample 7.

In an alternative embodiment the drive means 5 only allow the displacement of the sample holder 6 so that sequentially all samples are irradiated but do not allow for a translation during the irradiation.

A combination of the above precession movement and translation allows the normal to the sample plane to rotate about all possible axes in the plane of the sample, or all possible rotations about the centre of the sample surface except for in-plane rotation.

As will be apparent to the man skilled in the art the movement of the sample holder with respect to the radiation beam can be obtained using a source and detector which are held stationary while moving the sample holder or using a stationary samples holder and moving the source and detector, or by using a combined movement of the source and detector on the one hand and the samples holder on the other hand.

What is claimed is:

1. A method for successively performing a powder diffraction analysis of at least two powder samples being contained in sample holding means, wherein use is made of an apparatus comprising:

a source of radiation being adapted to direct a radiation beam to a powder sample, a detector for detecting diffraction radiation of a powder sample, a drive means for effecting a movement of an irradiated powder sample during irradiation and detection with respect to the radiation beam, wherein the method comprises the steps of:

irradiating a powder sample and detecting the diffraction radiation of the powder sample, arranging a further powder sample such that said radiation beam is directed to said further powder sample, and irradiating said further powder sample and detecting the diffraction radiation of said further sample, wherein during irradiation and detection of each sample the drive means effect a movement of the irradiated sample with respect to the radiation beam for the purpose of improving particle statistics, and wherein the sample holding means comprise a common multiple samples holder holding said at least two powder samples, wherein the drive means cause the common multiple samples holder to perform a precession movement with respect to the radiation beam during the step of irradiation and detection of a powder sample.

2. The method according to claim 1, wherein the drive means are connected to said common multiple samples holder.

3. The method according to claim 1, wherein said drive means are connected to radiation source and detector for the purpose of effecting the movement of the common multiple samples holder with respect to the radiation beam.

4. The method according to claim 1, wherein the source of radiation is an X-ray source.

5. The method according to claim 1, wherein the diffraction analysis is a transmission diffraction analysis.

6. The method according to claim 1, wherein said common multiple samples holder is a plate having an array of wells, each being well adapted to contain a powder sample.

7. A method for successively performing a powder diffraction analysis of at least two powder samples being contained in sample holding means, wherein use is made of an apparatus comprising:

a source of radiation being adapted to direct a radiation beam to a powder sample, a detector for detecting diffraction radiation of a powder sample, a drive means for effecting a movement of an irradiated powder sample during irradiation and detection with respect to the radiation beam, wherein the method comprises the steps of:

irradiating a powder sample and detecting the diffraction radiation of the powder sample, arranging a further powder sample such that said radiation beam is directed to said further powder sample, and irradiating said further powder sample and detecting the diffraction radiation of said further sample, wherein during irradiation and detection of each sample the drive means effect a movement of the irradiated sample with respect to the radiation beam for the purpose of improving particle statistics, and wherein the sample holding means comprise a common multiple samples holder holding said at least two powder samples wherein the drive means cause the common multiple samples holder to perform a combination of a precession movement and a translation with respect to the radiation beam during the step of irradiation and detection of a powder sample.

8. The method according to claim 7, wherein the source of radiation is an X-ray source.

9. The method according to claim 7, wherein the diffraction analysis is a transmission diffraction analysis.

10. The method according to claim 7, wherein said common multiple samples holder is a plate having an array of wells, each being well adapted to contain a powder sample.

11. The method according to claim 10, wherein said wells are arranged at a centre to centre distance of between 2 and 10 millimetres.

12. The method according to claim 7, wherein the drive means are connected to said common multiple samples holder.

13. The method according to claim 7, wherein said drive means are connected to radiation source and detector for the purpose of effecting the movement of the common multiple samples holder with respect to the radiation beam.

14. A method according to claim 7, wherein the diffraction is a transmission diffraction analysis, the radiation beam is a vertical beam, wherein the source of radiation is vertically above or vertically below the samples holder and the detector is vertically below or vertically above the samples holder, the samples holder being disposed between the source of radiation and the detector.

15. In combination an apparatus for performing a powder diffraction analysis of a powder sample and a sample holding means, wherein said apparatus comprises:

a source of radiation being adapted to direct a radiation beam to a powder sample in said sample holding means, a detector for detecting diffraction radiation of a powder sample, a drive means for effecting a movement of an irradiated powder sample therein during irradiation and detection with respect to the radiation beam, wherein during irradiation and detection of each sample the drive means effect a movement of the irradiated sample with respect to the radiation beam for the purpose of improving particle statistics, wherein the sample holding means comprise a common multiple samples holder holding said at least two powder samples, wherein the drive means cause the common multiple samples holder to perform a precession movement with respect to the radiation beam during the step of irradiation and detection of a powder sample.

16. The combination of claim 15, wherein the drive means are connected to said common multiple samples holder and wherein said drive means are adapted to effect, during irradiation and detection of a sample contained in said common multiple samples holder, a movement of said common multiple samples holder with respect to the radiation beam.

17. A method for successively performing a powder diffraction analysis of at least two powder samples being contained in sample holding means, wherein use is made of an apparatus comprising:

a source of radiation being adapted to direct a radiation beam to a powder sample, a detector for detecting diffraction radiation of a powder sample, a drive means for effecting a movement of an irradiated powder sample during irradiation and detection with respect to the radiation beam, wherein the method comprises the steps of:

irradiating a powder sample and detecting the diffraction radiation of the powder sample, arranging a further powder sample such that said radiation beam is directed to said further powder sample, and irradiating said further powder sample and detecting the diffraction radiation of said further sample, wherein during irradiation and detection of each sample the drive means effect a movement of the irradiated sample with respect to the radiation beam for the purpose of improving particle statistics, and wherein the sample holding means comprise a common multiple samples holder holding said at least two powder samples, and wherein the drive means are connected to said common multiple samples holder and wherein said drive means effect, during irradiation and detection of a sample contained in said common multiple samples holder, a movement of said common multiple samples holder with respect to the radiation beam, and wherein said movement of the common multiple samples holder includes a predetermined tilting of an axis perpendicular to a sample plane with respect to said radiation beam, wherein said movement includes a series of tilting movements of an axis perpendicular to a sample plane with respect to said radiation beam in combination with stepwise rotation of the common multiple sample holder.

18. A method for performing high-throughput transmission diffraction analysis of powder samples, comprising:
providing at least a first and a second powder sample in a common sample holder;
positioning said first powder sample with respect to a radiation beam;
after the positioning of the first powder sample, irradiating the first powder sample with the radiation beam directed substantially perpendicular to a sample plane and detecting transmission diffraction radiation of the first powder sample irradiated by the radiation beam, wherein the sample plane is substantially horizontal, and wherein the radiation beam is a substantially vertical beam;
during irradiation of the first powder sample and the detecting of the transmission diffraction radiation of the first powder sample, tilting the sample holder about an axis substantially parallel to the sample plane and translating the sample holder in the sample plane so as to translate the first powder sample in the sample plane with respect to the radiation beam;
after the irradiating of the first powder sample, the detecting of the transmission diffraction radiation of the first powder sample and the translating of the first powder sample, positioning the second powder sample with respect to the radiation beam;
after the positioning of the second powder sample, irradiating the second powder sample with the radiation beam directed substantially perpendicular to a sample plane and detecting transmission diffraction radiation of the second powder sample irradiated by the radiation beam; and
during irradiation of the second powder sample and the detecting of the transmission diffraction radiation of the second powder sample, tilting the sample holder about an axis substantially parallel to the sample plane and translating the sample holder in the sample plane so as to translate the second powder sample in the sample plane with respect to the radiation beam.

19. The method according to claim 18, wherein the translating of each powder sample during irradiating and detecting thereof is performed stepwise.

20. The method according to claim 18, wherein the radiation beam remains substantially perpendicular to the sample plane during the irradiating and the detecting.

21. The method according to claim 18, wherein the radiation beam includes X-rays.

22. The method according to claim 18, wherein the sample holder includes a plate having an array of wells, each well containing a powder sample.

23. The method according to claim 22, wherein said wells are arranged at a center to center distance between 2 and 10 millimeters.

24. The method according to claim 18, wherein the sample plane is substantially horizontal, and wherein the radiation beam is a substantially vertical beam.

25. The method according to claim 18, wherein said first and second sample are simultaneously prepared in said sample holder.

26. A method for performing high-throughput transmission diffraction analysis of powder samples, comprising:
providing at least a first and a second powder sample in a common sample holder;
positioning said first powder sample with respect to a radiation beam;
after the positioning of the first powder sample, irradiating the first powder sample with the radiation beam directed substantially perpendicular to a sample plane and detecting transmission diffraction radiation of the first powder sample irradiated by the radiation beam, wherein the sample plane is substantially horizontal, and wherein the radiation beam is a substantially vertical beam;
during irradiation of the first powder sample and the detecting of the transmission diffraction radiation of the first powder sample, translating the sample holder in the sample plane so as to translate the first powder sample in the sample plane with respect to the radiation beam, wherein the radiation beam is tilted with respect to an axis perpendicular to said horizontal sample plane during the irradiation of said first powder sample and the detecting of the transmission diffraction radiation of said first powder sample;
after the irraciating of the first powder sample, the detecting of the transmission diffraction radiation of the first powder sample and the translating of the first powder sample, positioning the second powder sample with respect to the radiation beam;
after the positioning of the second powder sample. irradiating the second powder sample with the radiation beam directed substantially perpendicular to a sample plane and detecting transmission diffraction radiation of the second powder sample irradiated by the radiation beam; and
during irradiation of the second powder sample and the detecting of the transmission diffraction radiation of the second powder sample, translating the sample holder in the sample plane so as to translate the second powder sample in the sample plane with respect to the radiation beam, wherein the radiation beam is tilted with respect to an axis perpendicular to said horizontal sample plane during the irradiation of said second powder samples and the detecting of the transmission diffraction radiation of said second powder samples.

27. A method for performing high-throughput transmission diffraction analysis of powder samples, comprising:
providing at least a first and a second powder sample in respective wells in a plate having an array of wells;
arranging said plate substantially horizontal to position said first powder sample with respect to a vertical radiation beam;
after the positioning of the first powder sample, irradiating the first powder sample with the radiation beam and detecting transmission diffraction radiation of the first powder sample irradiated by the radiation beam;

during irradiation of the first powder sample and the detecting of the transmission diffraction radiation of the first powder sample, tilting the sample holder about an axis substantially parallel to the sample plane and translating the plate in a horizontal plane to cause the first powder sample to follow a path with respect to the radiation beam;

after the irradiating of the first powder sample, the detecting of the transmission diffraction radiation of the first powder sample and the translating of the first powder sample, positioning the second powder sample with respect to the vertical radiation beam;

after the positioning of the second powder sample, irradiating the second powder sample with the radiation beam and detecting transmission diffraction radiation of the second powder sample irradiated by the radiation beam; and during irradiation of the second powder sample and the detecting of the transmission diffraction radiation of the second powder sample, tilting the sample holder about an axis substantially parallel to the sample plane and translating the plate in the horizontal plane to cause the second powder sample to follow a path with respect to the radiation beam.

28. A method for performing high-throughput transmission diffraction analysis of powder samples, comprising:
for each successive powder sample supported in a common sample plate:
positioning the powder sample with respect to a radiation beam directed substantially perpendicular to a sample plane, wherein the sample plane is substantially horizontal, and wherein the radiation beam is a substantially vertical beam;
irradiating the powder sample with the radiation beam;
detecting transmission diffraction radiation of the powder sample irradiated by the radiation beam; and
during the irradiating and the detecting, tilting the sample holder about an axis substantially parallel to the sample plane and translating the sample plate in the sample plane so as to translate the successive powder sample in the sample plane with respect to the radiation beam.

29. A device for performing high-throughput transmission diffraction analysis of powder samples, comprising:
a sample holder adapted to hold a plurality of powder samples;
a source of radiation adapted to direct a radiation beam toward one of the powder samples in the sample holder in a direction substantially perpendicular to a sample plane, wherein the sample plane is substantially horizontal, and wherein the radiation beam is a substantially vertical beam;
a detector adapted to detect transmission diffraction radiation of an irradiated powder sample; and
a drive adapted to translate, during irradiation of the powder sample and detection of the transmission diffraction radiation of the irradiated powder sample, the sample holder in the sample plane so as to translate the powder sample in the sample plane with respect to the radiation beam, and to tilt the sample holder about an axis substantially parallel to the sample plane during the irradiation and the detecting of the transmission diffraction radiation of said powder sample, and to move the sample holder to move successive powder samples into position for the irradiation, the detection and the translation.

30. A method for performing high-throughput transmission diffraction analysis of powder samples, comprising:
providing at least a first and a second powder sample in respective wells in a plate having an array of wells;
arranging said plate substantially horizontal to position said first powder sample with respect to a vertical radiation beam;
after the positioning of the first powder sample, irradiating the first powder sample with the radiation beam and detecting transmission diffraction radiation of the first powder sample irradiated by the radiation beam;
during irradiation of the first powder sample and the detecting of the transmission diffraction radiation of the first powder sample, tilting the radiation beam with respect to an axis perpendicularly to said horizontal sample plane and translating the plate in a horizontal plane to cause the first powder sample to follow a path with respect to the radiation beam;
after the irradiating of the first powder sample, the detecting of the transmission diffraction radiation of the first powder sample and the translating of the first powder sample, positioning the second powder sample with respect to the vertical radiation beam;
after the positioning of the second powder sample, irradiating the second powder sample with the radiation beam and detecting transmission diffraction radiation of the second powder sample irradiated by the radiation beam; and
during irradiation of the second powder sample and the detecting of the transmission diffraction radiation of the second powder sample, tilting the radiation beam with respect to an axis perpendicularly to said horizontal sample plane and translating the plate in the horizontal plane to cause the second powder sample to follow a path with respect to the radiation beam.

31. A method for performing high-throughput transmission diffraction analysis of powder samples, comprising:
for each successive powder sample supported in a common sample plate:
positioning the powder sample with respect to a radiation beam directed substantially perpendicular to a sample plane, wherein the sample plane is substantially horizontal, and wherein the radiation beam is a substantially vertical beam;
irradiating the powder sample with the radiation beam;
detecting transmission diffraction radiation of the powder sample irradiated by the radiation beam; and
during the irradiating and the detecting, tilting the radiation beam with respect to an axis perpendicularly to said horizontal sample plane and translating the sample plate in the sample plane so as to translate the successive powder samples in the sample plane with respect to the radiation beam.

32. A device for performing high-throughput transmission diffraction analysis of powder samples, comprising:
a sample holder adapted to hold a plurality of powder samples;
a source of radiation adapted to direct a radiation beam toward one of the powder samples in the sample holder in a direction substantially perpendicular to a sample plane, wherein the sample plane is substantially horizontal, and wherein the radiation beam is a substantially vertical beam;
a detector adapted to detect transmission diffraction radiation of an irradiated powder sample; and
a drive adapted to translate, during irradiation of the powder sample and detection of the transmission diffraction radiation of the irradiated powder sample, the sample holder in the sample plane so as to translate the powder sample in the sample plane with respect to the radiation beam, and to tilt the radiation beam with respect to an axis perpendicularly to said horizontal sample plane during the irradiation and the detecting of the transmission diffraction radiation of said powder sample, and to move the sample holder to move successive powder samples into position for the irradiation, the detection and the translation.

* * * * *